United States Patent [19]
Klein et al.

[11] 4,031,399
[45] June 21, 1977

[54] FLUOROMETER

[75] Inventors: Gerald Lee Klein, Orange; Richard C. Meyer, La Habra, both of Calif.

[73] Assignee: Beckman Instruments, Inc., Fullerton, Calif.

[22] Filed: Feb. 24, 1975

[21] Appl. No.: 552,653

[52] U.S. Cl. .......................... 250/461 B; 250/372; 356/85

[51] Int. Cl.² ........................................ G01M 21/38

[58] Field of Search .......... 250/373, 492, 358–360, 250/372, 461; 356/51, 85; 313/344

[56] References Cited

UNITED STATES PATENTS

| | | | |
|---|---|---|---|
| 2,007,920 | 7/1935 | Braselton | 313/344 |
| 2,123,573 | 7/1938 | McFarlan et al. | 250/372 |
| 2,146,579 | 2/1939 | Inman | 313/344 |
| 2,631,243 | 3/1953 | Weber et al. | 250/365 |
| 2,834,247 | 5/1958 | Pickels | 250/372 |
| 3,105,908 | 10/1963 | Burkhardt | 250/372 |
| 3,457,407 | 7/1969 | Goldberg | 250/373 |
| 3,486,829 | 12/1969 | Wilks | 356/51 |
| 3,806,256 | 4/1974 | Ishak | 350/96 |
| 3,814,939 | 6/1974 | Parker et al. | 250/373 |

*Primary Examiner*—Harold A. Dixon
*Attorney, Agent, or Firm*—R. J. Steinmeyer; R. R. Meads; J. R. Shewmaker

[57] ABSTRACT

A fluorometer for analyzing a sample by detecting light induced radiation emitted from the sample including apparatus for generating a narrow slit of light in the plane of the sample and transfer apparatus including a light shield having an acutely angled port immediately adjacent the sample for collecting radiation emitted by the sample and transmitting same via a light pipe to a remote detector.

4 Claims, 4 Drawing Figures

FLUOROMETER

BACKGROUND OF THE INVENTION

1. Field of the Invention

This invention relates to fluorometers and, more particularly, to a fluorometer which detects radiation emitted by a sample in response to a small area of light striking the sample.

2. Description of the Prior Art

Fluorometers have been widely adopted in laboratory and clinical analysis to identify and study the behavior of numerous materials and biological substances. A fluorescent sample absorbs light of a given wavelength and, in response thereto, emits light of a different wavelength. Often the efficiency of absorption and emission is low so that fluorometers of increasing sensitivity to emitted radiation are required for reliable analysis. As sensitivity is increased, however, the probability also increases that radiation from extraneous sources or from the excitation source will adversely affect detection of the radiation issuing from the sample.

Presently available fluorometers, which flood a sample using an ultraviolet source or which image a slit of light of a desired bandwidth on the sample, either lack the versatility to collect and detect the desired fluorescent radiation to the exclusion of radiation from other sources or are so complex and expensive in construction as to be impractical for many purposes. In this regard, by flooding a sample with ultraviolet light, all flourescent materials in the vicinity of the sample, such as nearby samples or extraneous materials, will fluoresce. As a result, extensive light baffling and shielding is employed to prevent this unwanted radiation from reaching the detector. Imaging a slit of light of a desired bandwidth on the sample in the past has involved complex arrangements of dispersive elements, such as optical prisms or gratings, which generally result in relatively low excitation energy levels and thus require more powerful radiation sources. Moreover, in both of the above approaches, in order to minimize entry of stray light into the system and to increase the system sensitivity to emitted radiation, the detector is either placed adjacent the sample being analyzed or is remotely located only if a complex optical system is employed between the sample and the detector.

SUMMARY OF THE INVENTION

The present invention resides in a new and improved fluorometer having increased sensitivity to radiation emitted from a sample material which overcomes the disadvantages of the prior systems and which achieves this increased sensitivity in a commercially practical form that is relatively simple, compact, and inexpensive in construction and reliable in operation.

More specifically, a preferred embodiment of the fluorometer utilizes an excitation system for imaging a small area of light in the plane of the sample to be analyzed and includes apparatus for transferring radiation emitted by the sample to a remote detector. In the preferred form, the transfer apparatus includes an opaque light shield having a port situated immediately adjacent the sample on the side of the sample plane receiving the slit of light to collect a sector of the radiation emitted by the sample. The emitted radiation intercepted by the port is collected by a light pipe having an end thereof positioned within the port and transmitted thereby to the remote detector.

DESCRIPTION OF THE PREFERRED EMBODIMENT

Figure 1:
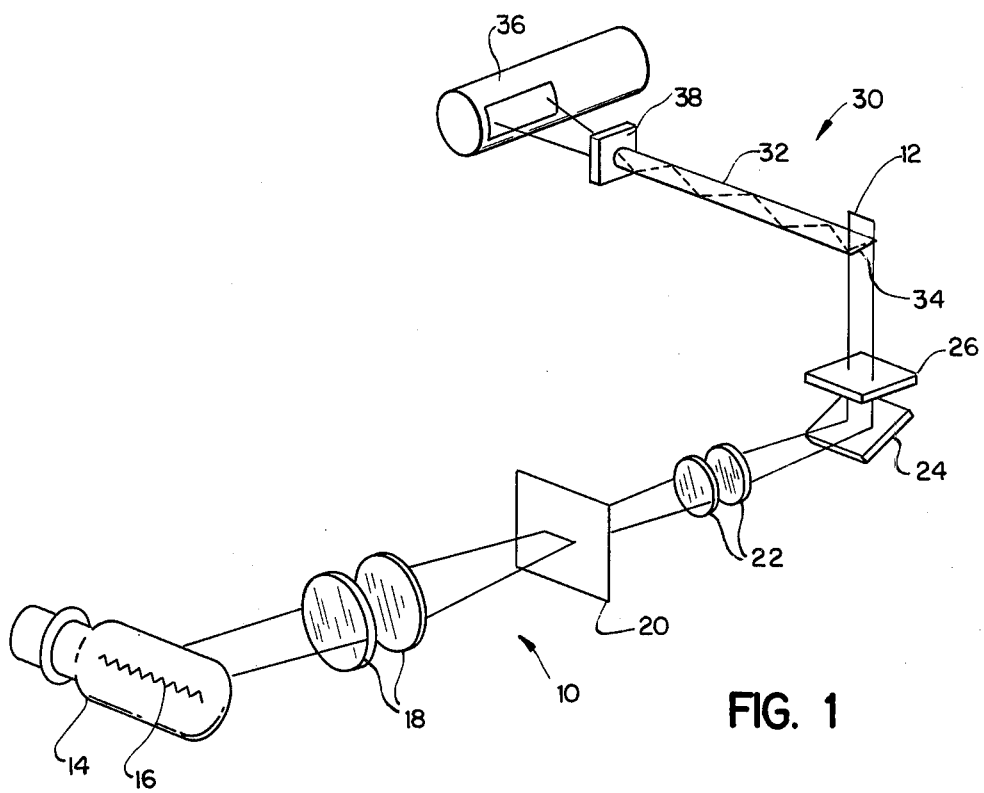
FIG. 1 is an optical diagram of the fluorometer of the present invention.

As shown in the drawings for purpose of illustration, and in particular FIG. 1 thereof, the present invention is embodied in a fluorometer for energizing a fluorescent sample with light energy and detecting radiaton emitted by the sample. The fluorometer includes an excitation system, indicated generally by the numeral 10, for generating a small area of light, such as a narrow slit 12, which is imaged in the plane of the sample to be analyzed so that the slit of light strikes the sample. The sample (not shown in FIG. 1) may be mounted or positioned in the fluorometer in conventional fashion. For example, the sample may be carried by a glass or plastic slide which is mounted to register the sample at the slit 12. A carriage or other transport device may be employed to move the sample into registry with the slit. A plurality of samples carried by one or a plurality of slides may be advanced by the carriage past the slit for analysis on a sequential basis.

The excitation system 10 includes a tungsten source lamp 14 with filament 16, a pair of condensing lenses 18, a slit plate 20, a pair of objective lenses 22, a diagonal mirror 24, and a primary filter 26, all of conventional construction. The condensing lenses 18 focus a reduced image of the source lamp filament 16 onto the slit plate 20. The objective lenses 22 together with mirror 24 transfer a sharp image of the illuminated slit in plate 20 to the plane of the sample. The desired band of wavelengths for exciting the sample is selected by the primary filter 26 which has a pass band corresponding to the desired wavelengths. In order to analyze a variety of samples, it is desirable that filter 26 be readily replaceable with filters having different pass band characteristics depending upon the particular sample of interest.

In accordance with the present invention, a light transfer apparatus, illustrated generally by the numeral 30, is positioned immediately adjacent the sample to collect radiation emitted by the sample and to transmit the radiation to a remote detector. The transfer apparatus includes a light pipe 32 having an angled end surface 34 positioned immediately adjacent the sample and the opposite end thereof facing a detector 36 such as a photomultiplier tube. A secondary filter 38 is positioned in the transfer system 30 between the light pipe and the detector to ensure that only radiation emitted from the sample is transferred to the detector. To this end, the secondary filter has a band pass characteristic which rejects wavelengths generated by the excitation system 10.

Figure 2:
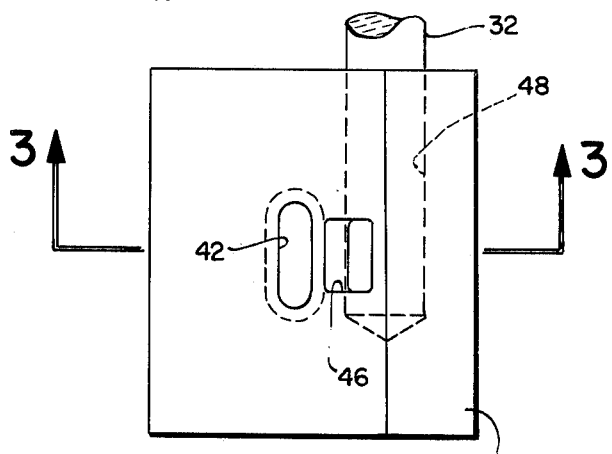
FIG. 2 is an enlarged top plan view of a light transfer shield utilized in the optical system of FIG. 1.
Figure 3:
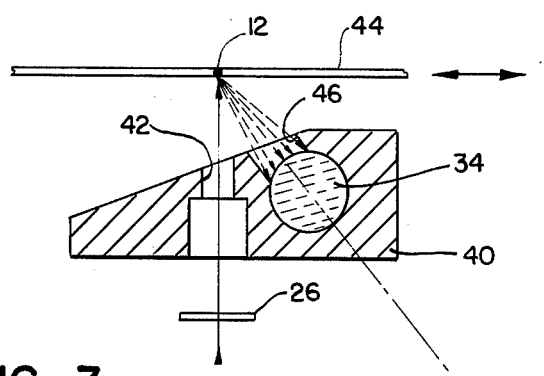
FIG. 3 is a cross-sectional view, taken generally along line 3—3, of the shield of FIG. 2.

The transfer apparatus 30, as illustrated in FIGS. 2 and 3 also includes an opaque light shield 40 positioned closely adjacent the plane of the sample to be analyzed. The light shield is not illustrated in FIG. 1 for the sake of clarity. The light shield 40 includes an opening 42 through which the light slit 12 from excitation system 10 is imaged onto the plane of the sample. The slit 12 extends into FIG. 3 and is shown simply as a point of light. The sample plane, illustrated generally by numeral 44, may comprise a slide carrying one or more samples which is moved in the direction of the arrow to position the samples at the location of the light slit 12. Use of the narrow, focused slit of light to energize the samples ensures that only the sample of interest is energized and only a certain zone of such sample if desired. The opening 42 in shield 40 is dimensioned such that the image of slit 12 is passed by the shield but stray images in the optial system are blocked by the shield.

The light shield 40 further includes a port 46 adjacent opening 42 and facing the plane of the sample for intercepting a sector of the radiation emitted by the sample. Port 46 has a longitudinal axis intersecting the sample plane at an acute angle. Port 46 communicates with a passage 48 extending perpendicularly thereto within the light shield. One end of light pipe 32 is secured within passage 48 with the angled end surface 34 of the light pipe positioned at the intersection of the port 46 and the passage 48 to receive the radiation intercepted by the port and redirect it within the light pipe toward the detector 34.

Figure 4:
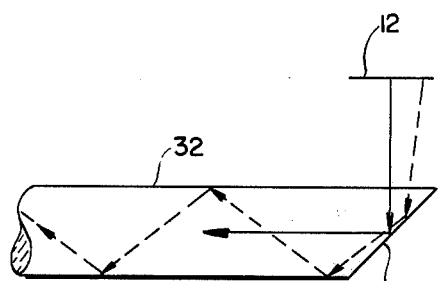
FIG. 4 is a fragmentary, side elevational view of the light pipe utilized in the fluorometer of FIG. 1.

Light pipe 32 is fabricated from a suitable light transmissive material which exhibits no fluorescence in the excitation wavelength band of interest. One end of the pipe is cut and polished at a 45° angle with respect to the pipe longitudinal axis to form surface 34 while the other end is cut and polished at 90. The collection of radiation issuing from the sample by the light pipe is illustrated in FIG. 4. Radiation from the area of the sample exposed to the slit 12 which enters the pipe perpendicular to the axis thereof is internally reflected by the angled end surface 34 and directed toward the other end of the pipe parallel to the axis thereof. Radiation entering other than perpendicularly (illustrated by dashed line) is likewise directed to the other end of the pipe by internal reflections from surface 34 and from the wall of the pipe. As a result, radiation intercepted by port 46 is collected by the light pipe and transmitted therein toward the detector 36. Preferably, the light pipe is covered with an opaque material to block the entry of stray or other extraneous light.

From the foregoing, it will be evident that the present invention provides a novel fluorometer which is extremely sensitive and of simple construction. Radiation emitted from the sample is collected at a location immediately adjacent the sample on the same side of the sample plane as the excitation light striking the sample. This maximizes the energy collected to increase the system sensitivity. Moreover, it minimizes errors due to quench, i.e. reabsorption of radiation by either the sample or the sample carrier (slide). In addition, errors due to back scattering of excitation energy are minimized by secondary filter 38 which rejects wavelengths generated by the excitation system 10. Also, the increased sensitivity of the fluorometer permits the use of a tungsten radiation source 14 as a source of ultraviolet radiation. Such tungsten sources are generally unsuitable as ultraviolet sources due to their relatively low ultraviolet emission. It will also be apparent that while a preferred embodiment of the invention has been illustrated and described, various modifications may be made therein without departing from the spirit and scope of the invention as defined by the appended claims.

What is claimed is:

1. A fluorometer comprising:
means for generating a small area of light of a first bandwidth in a plane of a sample to be analyzed, said sample emitting radiation of a second bandwidth in response to said light striking said sample;
transfer means on a side of said plane receiving said light and immediately adjacent said sample for collecting radiation emitted from said sample and for transmitting said radiation to the exclusion of said light to a detector remote from said sample for analysis, said transfer means comprising an opaque light shield including a port immediately adjacent said sample and including a longitudinal axis defining an acute angle with said plane and being dimensioned to receive and collect a sector of the radiation emitted from said sample, and a light pipe mounted in said shield with an acutely angled end in said port to intersect said longitudinal axis and an opposite end remote from said sample and facing said detector; and
a radiation filter for only passing radiation of said second bandwidth, said filter being located at said opposite end of said light pipe and adjacent said detector.

2. The fluorometer of claim 1 wherein said light shield includes an opening adjacent said port dimensioned to pass said light from a source to said plane of said sample while stray images in the generating means are blocked by said shield.

3. The fluorometer of claim 1 wherein said generating means includes aperature means and means for focusing light from a source on a predetermined aperture in said aperture means and means for projecting a sharp image of said predetermined aperture in said plane of said sample.

4. The fluorometer of claim 3 wherein said source is a tungsten filament lamp.

* * * * *